United States Patent [19]

Waldorf et al.

[11] Patent Number: 5,137,345
[45] Date of Patent: Aug. 11, 1992

[54] APPARATUS FOR MONITORING PHYSIOLGICAL DATA TO DETECT DRUG IMPAIRMENT

[75] Inventors: Ronald A. Waldorf, Los Angeles; Barbara J. Mauch, Inglewood, both of Calif.

[73] Assignee: Oculokinetics, Inc., Torrance, Calif.

[21] Appl. No.: 700,445

[22] Filed: May 15, 1991

[51] Int. Cl.$^5$ .............................................. A61B 3/14
[52] U.S. Cl. ..................................... 351/206; 351/221
[58] Field of Search ................ 351/205, 206, 209-213, 351/221, 243; 128/745

[56] References Cited

U.S. PATENT DOCUMENTS

| | | | |
|---|---|---|---|
| 3,782,364 | 1/1974 | Watt | 351/209 |
| 4,815,839 | 3/1989 | Waldorf | 351/210 |
| 4,988,183 | 1/1991 | Kasahara et al. | 351/206 |
| 5,070,883 | 12/1991 | Kasahara | 351/209 |

Primary Examiner—Rodney B. Bovernick
Assistant Examiner—James Phan
Attorney, Agent, or Firm—Michael A. Painter

[57] ABSTRACT

A non-invasive apparatus for monitoring physiological responses for detecting the presence of drug impairment. The oculomotor and pupillary system is monitored and evaluated to detect the ingestion of drugs and the impairing effect or influence thereof. The horizontal, vertical, oblique and torsional eye movement, eye lid blink activity as well as the size and reactivity of the pupil are the primary data sources. An enclosed chamber surrounds each of the eyes of the subject, and thereby precludes the admission of ambient light. Within each chamber are disposed point sources of infrared radiation specifically oriented with respect to the subject's eye. An infrared sensitive video camera is positioned to minimize the effect of cosine compression within each chamber relative to the subject and is positioned with respect to the infrared radiation sources in order to provide maximum contrast between the pupil and iris of the eye. To detect movement of the eye in response to visible stimulus, a plurality of low intensity, visible light sources are disposed horizontally and vertically within each chamber. The sequential illumination of the visible light sources simulates eye movement while precluding pupil reaction thereto. The output of the video camera is processed concurrently with data responsive to other physiological responses to determine drug impairment.

11 Claims, 2 Drawing Sheets

APPARATUS FOR MONITORING PHYSIOLGICAL DATA TO DETECT DRUG IMPAIRMENT

BACKGROUND OF THE INVENTION

1. Field of the Invention

The present invention generally relates to apparatus used to detect drug impairment, and more particularly to those systems with infrared illumination which monitor eye movement, eye lid blinking and pupil reaction to sources of radiation in the visible portion of the optical spectrum.

2. Prior Art

There are numerous devices and methods disclosed by the prior art which are used for analyzing physiological data in general, and eye movement in particular, as a diagnostic tool in the clinical investigation of organic disorders or drug impairment. It is understood the term "impairment" is intended to refer to the diminishing in strength, value, quantity or quality of the performance of activities of an individual. In recent years, a number of devices and methods have been disclosed which are specifically oriented to the detection, evaluation and analysis of disorders caused by ingestion of drugs and the resulting physiologic changes caused thereby. Throughout this application, reference is made to the effects of impairment by drugs. It is understood the term "drugs" includes not only medicinal substances and addictive narcotics, but also is to be understood to include any other ingested substance which affects the brain, as well as alcoholic beverages and the like. The techniques which are disclosed by the prior art are generally identified as electronystagmography (ENG), electro-oculographic (EOG), photoelectronystagmography (PENG) and Frenzel lenses.

There is a general consensus that eye movement may be employed as indicia for determining the sensory and motor aspects of the oculomotor system. This principle is made use of by stimulating the eye or eyes in some manner and evaluating the eye response to such a stimulus. Nystagmus is involuntary movement of the eyes. The nystagmus of the human eye will vary depending upon the organic disorder or the cause thereof. In measuring nystagmus, the devices disclosed by the prior art (ENG and EOG) use the inherent electrical potential between the cornea and the retina of the eye (the corneal-retinal potential) as a means for recording eye movement. This technique is based on the fact the eye acts as an electric dipole with the cornea being positively charged relative to the retina. The dipole axis is said to correspond to the visual axis. In the devices taught by the prior art, electrodes are placed at the skin surface adjacent to the eye orbit in an attempt to indirectly measure changes in electrical potential. The potential changes resulting from eye movement are recorded on various types of polygraph instruments. An ENG system uses a time constant and is generally used to record eye movement, whereas eye positions as well as eye movements are recorded using an EOG system.

Both the ENG and EOG systems exhibit inherent problems. Skin potential responses are in the same general frequency band as the eye movements, and some subjects produce signals having greater amplitudes than the corneal-retinal potential. The second problem is incident to the polarization of the skin electrodes which causes baseline shifts in the recorded corneal-retinal potential. This may inhibit or even prevent the detection and recording of resulting eye movements. In both cases, detection and evaluation of eye lid blinks is, at best, extremely difficult.

Some of the electronic problems associated with ENG and EOG recording methods are overcome with the system defined as PENG. This technique, using infrared sensitive photoelectric cells mounted on goggles, is able to detect the difference in reflected light off the sclera relative to the iris. The difference in reflectivity during eye movement is translated into an electrical signal which can be recorded on a polygraph instrument similar to that used with ENG or EOG methods. With this technique, the problem of electropolarization or skin potential responses is eliminated as no connection is made to the skin. However, eyelid tremor and blinking still cause artifacts which complicate the analysis of the polygraph traces. The major disadvantage of PENG is that testing must be done with the eyes open and in some cases, the infrared light used was of a shorter wave length and thus could be seen by the patient after a period of dark adaptation. The visible light source provides a target for optic fixation which may reduce or inhibit the nystagmus. The problem of resolving eye position and blink responses with PENG is the same as that encountered with electro-techniques.

A number of the devices and methods taught by the prior art utilize the accepted principle that drug ingestion may affect nystagmus. One of the methods taught by the prior art is set forth in the U.S. Pat. No. 4,576,184. The method taught in the '184 patent comprises the steps of placing electrodes of an ENG device on the face of the subject and thereby record the corneal-retinal potential and/or brainwaves caused by drug ingestion, recording the resting eye movement activity of the subject during a static positional test and then comparing the resulting waveform with those which are purportedly characteristic of ingestion of different drugs. The problems with this device are inherent in the manner in which the waveforms are detected. Rather than directly monitoring eye movement and pupil reaction to optic stimuli, the method employs the indirect measurement of the potential difference between the cornea and retina of the eye. As stated hereinabove, this method introduces factors which can mitigate the effectiveness of measurement and detection of drug impairment. In addition to other inadequacies, the device taught by the '184 patent cannot be used to detect and analyze eye lid blink activity.

Another device taught by the prior art is set forth in Applicant's U.S. Pat. No. 4,815,839. The device taught in the '839 patent employs an infrared camera to monitor the movement of the eye upon being bathed in fully dispersed infrared radiation. As with the present invention, the device taught in this patent precludes the impingement of ambient light to prevent optic fixation. The problems inherent in this device relate to the dispersement of the impinging infrared radiation and the limitations imposed by the manner in which the pupil and eye of the subject are monitored. Using a fully dispersed source of infrared radiation will degrade the ability of monitoring the pupil of the eye. A video camera sensitive to infrared radiation will detect a diffused reflection of energy across the entire surface of the cornea resulting in a reduced contrast between the pupil and the adjacent elements, i.e., the pupil will appear to be visually lighter than absolute black. Under such conditions, objects that do not reflect light such as eyelashes and eyelid makeup, may appear to be darker than the pupil of the subject. Since measurement of the pupil was not an object of the device taught in the patent, the problem could be ignored.

The present invention solves the problems inherent in those taught by the prior art by appropriately positioning point-sources of infrared radiation relative to the monitoring camera and thereby preclude detection of reflected energy in the pupil area. For example, in measuring physiologic data relative to detecting influences from drugs, the lateral and downward displacement of the infrared sensitive camera allows full monitoring of the pupil along its horizontal axis. This offsets the effect of cosine compression to the region of eye motion that is of minimal importance. The monitored data is directly converted into signal indicia responsive to pupil size and position.

SUMMARY OF THE INVENTION

The present invention comprises an apparatus to monitor physiological data to detect drug impairment. Although it is understood the present invention monitors physiological data related to blood pressure, pulse rate, temperature and the like, emphasis is placed on pupil reaction, eye movement and eye lid blinks. A viewport housing is mounted upon an adjustable fixture in order to provide a stable base for monitoring eye movement. The viewport housing is separated into two visually isolated chambers separating the field of vision of the subject's eyes. The viewport housing is adapted to preclude impingement of ambient light upon the eyes of the subject. Within each chamber are mounted infrared light emitting sources which transmit a defined beam of infrared radiation at the pupil of the subject's eye. The interior of the chambers are coated with an energy absorbent surface to prevent the dispersal of radiated energy. A video camera sensitized to monitor infrared radiation is laterally displaced from the central axis of the viewport housing and is oriented to have an undistorted view of the pupil and preclude monitoring reflected infrared radiation impinging upon the eye of the subject. The output of the video camera is converted to an electrical signal which is responsive to the relative shading of the sclera, iris and pupil as well as any relative change in size thereof. The converted video signal as well as data responsive to pulse rate, blood pressure, temperature and other physiological indicia are processed by a digital computer relative to establish standards for measuring these physiological responses to drug ingestion. The output of the digital processor is coupled to recording equipment for real time observation or off-line analysis of the observed data and results of processing same.

It is therefore an object of the present invention to provide an improved apparatus for observing, recording and analyzing physiological data.

It is another object of the present invention to provide an apparatus for monitoring and recording data relative to the shading and movement of eye components.

It is still another object of the present invention to provide an apparatus for observing and recording physiological data which is responsive to drug ingestion.

It is still yet another object of the present invention for monitoring physiological data and detecting impairment from influences of drugs which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

DESCRIPTION OF THE PRESENTLY PREFERRED EMBODIMENT

Figure 1:
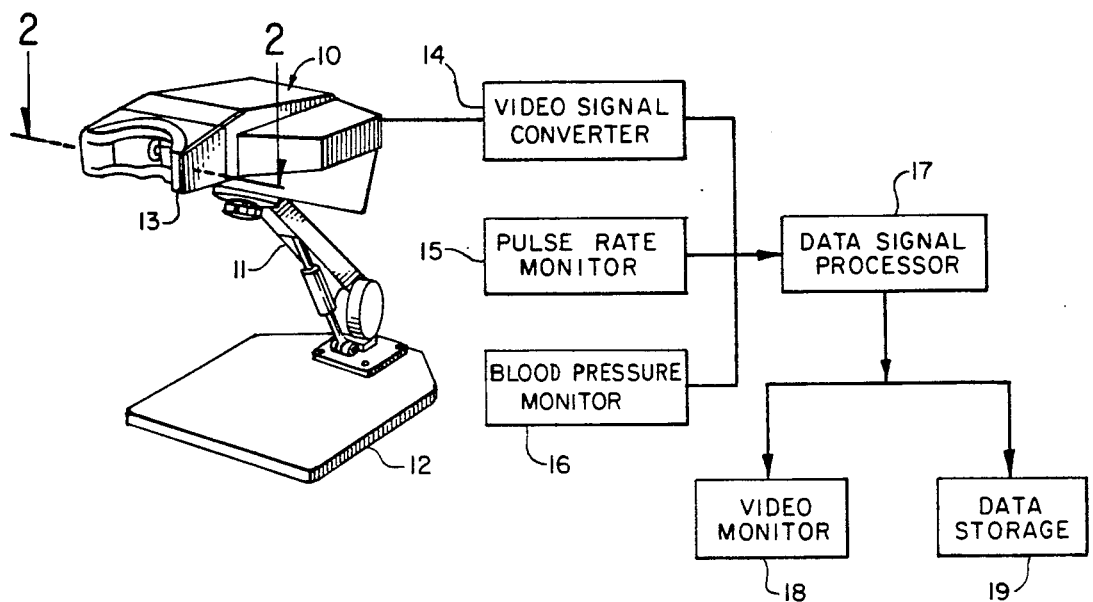
FIG. 1 illustrates the preferred embodiment of the present invention utilizing monitors for sensing eye movement, pulse rate and blood pressure.

An understanding of the present invention can be best gained by reference to FIG. 1 wherein a schematic block diagram of the invention is illustrated. The present invention monitors and analyzes the physiological responses of a subject to detect drug impairment. Use of the term drug impairment is understood to refer to the intoxicating influences as defined by diminishment in strength, value, quantity or quality of performance of an activity by the human being as a result of ingesting medicine, an addictive narcotic, alcoholic beverages or the like. The human responses include pulse rate, temperature, blood pressure and, most importantly, eye movement, eye lid blinks and pupil characteristics. As shown in FIG. 1, to measure the physiological responses to the subject's eye, a viewport housing 10 is supported upon an adjustable elevation fixture 11 all supported upon base 12. In making the appropriate measurements regarding the subject's eye, viewport housing 10 must be stable and thereby retard the movement of the subject. Viewport housing 10 incorporates viewing shield 13 which is adapted to tightly engage the face of the subject and thereby create a seal which precludes the impingement of ambient light upon the eyes of the subject.

As will be described hereinbelow, cameras used to monitor the subject's eyes are mounted within viewport housing 10. The output of the video cameras is processed by video signal converter 14 to produce electrical signals which are responsive to the movement and size of elements of the subject's eyes. In a like manner, pulse rate monitor 15 and blood pressure monitor 16 are used to measure and produce electrical signals responsive to the measured physiological data. Although FIG. 1 illustrates the measurement of only a limited number of physiological characteristics, it is understood that other relevant data may be monitored and used to detect and analyze drug impairment. The output of video converter 14, pulse rate monitor 15 and blood pressure monitor 16 are coupled to digital computer 17 which is implemented through a conventional digital computer such as an IBM-AT/XT personal computer. To provide for analysis of the processed data, data signal processor 17 is coupled to a video monitor 18 and a conventional data storage member 19 (e.g., a video tape recorder) thereby providing the ability to perform off-line or real-time analysis. As will be described hereinbelow, digital computer 17 also directly controls detection conditions such as stimulus position and/or intensity within viewport housing 10.

Figure 2:
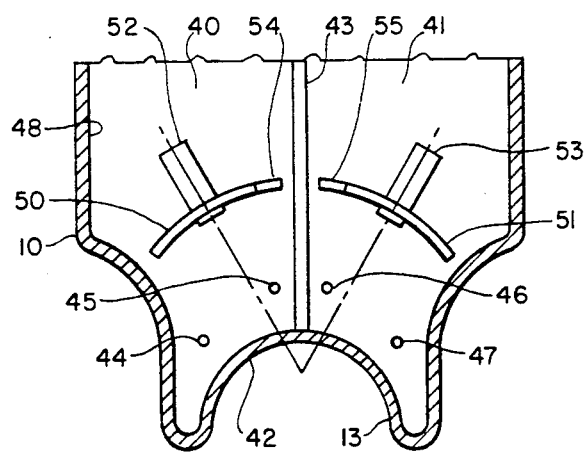
FIG. 2 is a partial, cross-sectional view of the view port housing shown in FIG. 1 taken through line 2—2 of FIG. 1.
Figure 3:
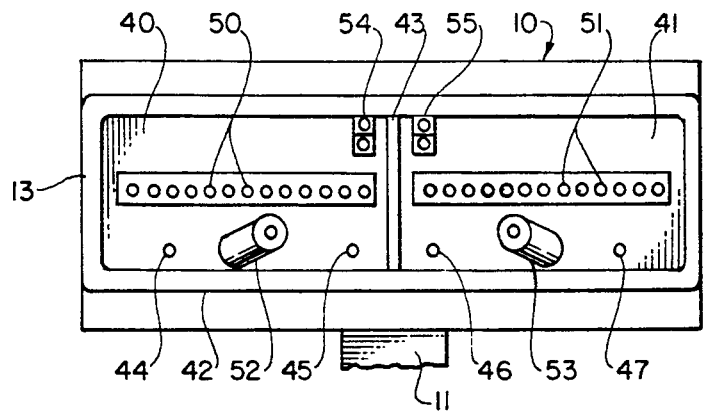
FIG. 3 is a front elevation view of the view port housing shown in FIG. 2.
Figure 4:
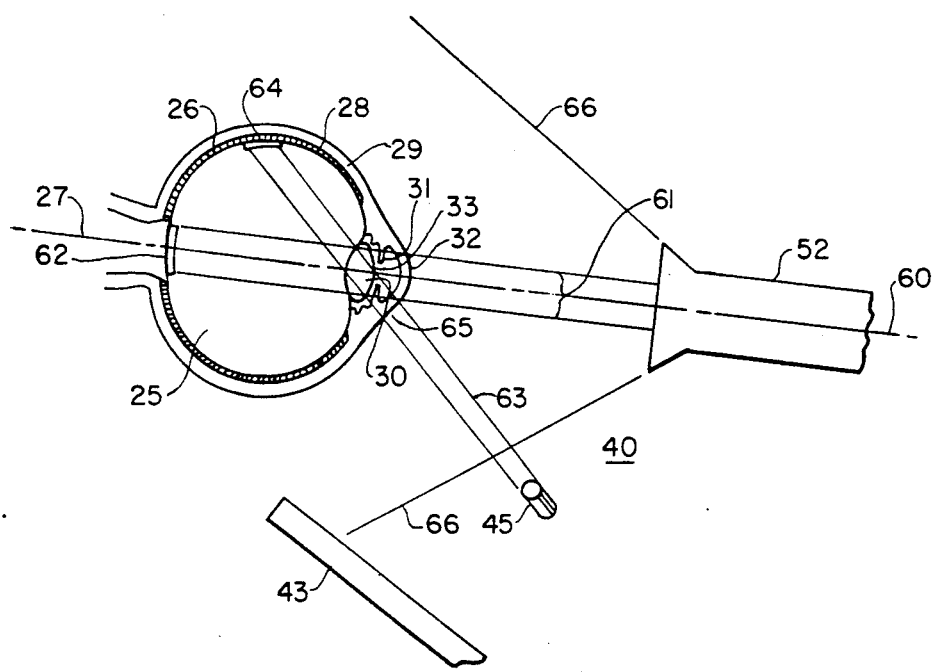
FIG. 4 is a schematic diagram of the human eye in relationship to a source of infrared radiation and an infrared sensing camera in accordance with the present invention.
Figure 5:
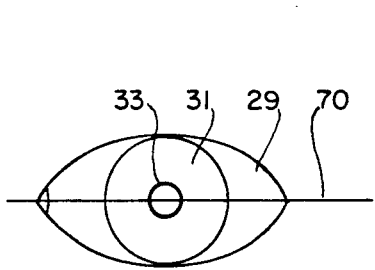
FIG. 5 is an anterior view of the eye elements monitored by the present invention.

Although an object of the present invention is to utilize a variety of sources of physiological data to analyze and detect drug impairment, the principal data analyzed are those resulting from the movement and/or characteristics of the subject's eye. An understanding of the structure used to monitor the subject's eyes can be best gained by reference to FIGS. 2, 3 and 4. It is an object of the present invention to not only monitor the movement and eye lid blink activity of the eye in response to stimuli, the present invention also provides for a qualitative and quantitative analysis of the pupil. An anterior view of a human eye is shown in FIG. 5. This is representative of the image which will be seen at video monitor 18. The interior structure of an eye is shown in FIG. 4. The central core comprises a vitreous body 25. The light sensitive retina 26 lines the inner surface of the eyeball and is connected to the optic nerve 27. The choroid 28 is a vascular coating which lies between the retina 26 and the sclera 29. The lens 30 lies along the optic axis and is capable of focusing incident light on the photosensitive retina. The iris 31 is the round, contractile membrane situated between the cornea 32 and the lens 30 and is perforated by the pupil 33. In achieving the objectives of the present invention, the present invention monitors horizontal and vertical gaze nystagmus, the size of the pupil 33 as well as any changes in size or reactivity thereof in response to stimuli, including eye lid blink activity.

Viewport housing 10 is bisected into a pair of visually isolated chambers 40 and 41 which are mirror images of one another. When the subject is in position against the surface 42 of viewing shield 13, the seal between the subject and surface 42 will preclude the impingement of ambient light into chambers 40 and 41. Chambers 40 and 41 are isolated from each other by an opaque interior panel 43.

The present invention provides for monitoring eye movement, pupil size and reactivity as well as blink characteristics through the radiation of energy in the infrared range. Infrared energy is radiated at wave lengths beyond the red end of the spectrum of visible light. Infrared radiation is beyond the visible range of the human eye. The preferred form of the present invention employs four infrared radiating members 44, 45, 46 and 47 which are typically implemented through the use of infrared light emitting diodes which produce a narrow beam of infrared radiation. As stated previously, to achieve a primary objective of the present invention, it is necessary to avoid dispersement of infrared radiation within interior chambers 40 and 41. To achieve this objective, the interior surface 48 of viewport housing 10 is coated with a flat-black, radiation absorbing membrane. Under these conditions, when the infrared light emitting diodes 44-47 are activated, a controlled beam of infrared energy will be projected specifically toward a selected target area while avoiding reflected energy which would otherwise reduce the effectiveness of the invention.

The present invention can apply visual stimulus to the subject's eye by producing a source of light in the visible range of the spectrum. As can be seen best in FIG. 2 and FIG. 3, a horizontal target presentation panel 50 comprising a plurality of light emitting members are mounted within chamber 40, a similar horizontal target presentation panel 51 being mounted within chamber 41. Panels 50 and 51 provide a low intensity moving target presentation system in the visible range of the spectrum. The intensity of the radiated visible light energy is controlled by digital computer 17 and maintained at a sufficiently low level to avoid reaction to pupil 33. The object of the horizontal target presentation panels 50 and 51 is to provide controlled movement of the subject's eye (i.e. sequential activation by digital computer 17) which can be monitored through the application of infrared radiation for detection by video cameras 52 and 53 which are sensitized to energy in the infrared range. Although it is understood the preferred embodiment of the present invention employs a pair of video cameras 52 and 53, a single video camera and reflective surfaces may be used to reflect images from either interior chambers 40 and 41 to the plane of the video camera sensor. Vertical target presentation panels 54 and 55 provide low intensity light in the visible range to provide for additional controlled movement of the eye.

An objective of the present invention is to properly orient video cameras 52 and 53 with respect to the subject as well as to the sources of infrared radiation 44-47, inclusive. For example, for the application of this technology for detection of impairment by drug ingestion, video cameras 52 and 53 are mounted beneath the horizontal target presentation panels 50 and 51. As can be seen best in FIG. 2, video cameras 52 and 53 are laterally displaced from the plane of interior panel 43. The lateral displacement of video cameras 52 and 53 are intended to minimize the effects of what is generally referred to as "cosine compression." If the pupil 33 is viewed along its optic axis, its rotation away from the plane of the camera lens would result in a decrease in the number of video camera sensing pixels per degree of angular rotation. As stated, this is a phenomenon generally referred to as cosine compression. In order to maximize the number of video camera sensing pixels per degree of eye movement in the area of interest, video cameras 52 and 53 are laterally displaced from interior panel 43 by 20° of arc. By displacing video cameras 52 and 53 by 20° of arc, the cameras will be in position to record eye movements which occur as the iris 31 and pupil 33 rotate thereby providing maximum resolution in terms of CCD pixel counts per degree of eye movement.

To maximize the contrast of the pupil 33 relative of the iris 31, etc., avoiding the dispersal of infrared radiation throughout chambers 40 and 41 is essential. For this purpose, infrared LED's 44, 45, 46 and 47 provide point sources of infrared radiation. It is understood that a point source of infrared radiation will result in a narrowly defined reflection or "hot spot" coincident with the image viewed by the cameras. FIG. 4 schematically depicts the relative placement of video camera 52 relative to interior panel 43 and light emitting diode 45.

The total field of view of camera 52 is generally designated by the reference numeral 66. The center of the field of view 66 of video camera 52 generally lies along optic axis 60. The area of interest in the field of view 66 of video camera 52 and the area of the retina 26 falling within the area of interest in the field of view are schematically identified by the reference numerals 61 and 62, respectively. By using a point source of infrared radiation which is directed outside of the area of interest in the field of view 61 and 62 of camera 52, observation of the eye can be carried out without regard to reflected energy. As shown in FIG. 4, infrared LED 45 directs its beam of infrared radiation schematically along path 63 illuminating an area of retina 26 identified by the reference numeral 64. Neither retina area 64 nor cornea section 65 are within the area of interest in the field of view 61 or are part of the viewed retina area 62. Although this discussion has referred solely to infrared LED 45, it is understood the same principle applies to infrared LED's 44, 46 and 47, and their respective orientation with respect to video cameras 52 and 53.

Figure 6:
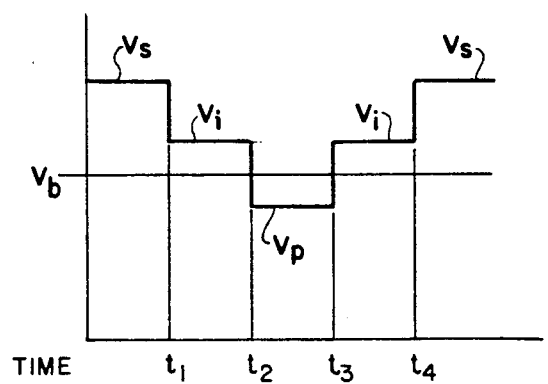
FIG. 6 is a waveform diagram reflecting relative shading and size of the sclera, iris and pupil shown in FIG. 5 as monitored in accordance with the present invention.

FIG. 5 illustrates an anterior view of a subject's eye as it would be seen by video monitor 18. FIG. 6 represents a waveform diagram representing an exemplary analysis which can be made from observable data. It is understood FIG. 6 is for the purpose of example only and is not intended to limit the manner in which the present invention detects, utilizes or analyzes recorded information. Bisecting the image of the eye shown in FIG. 5 along scan line 70, the waveform appearing in FIG. 6 is an analysis of the relationship of the sclera 29, iris 31 and pupil 33 along scan line 70. Selecting an arbitrary base line voltage $V_b$, and scanning the image of FIG. 5 from left to right, the waveform can be analyzed with respect to size and shape. $V_s$ represents a scan through the left portion of sclera 29. At time $t_1$, the scan passes from sclera 29 ($V_s$) to the darker iris ($V_i$); at $t_2$ the scan passes from the iris 31 to the black pupil 33 ($V_p$). In a like manner, at time $t_3$, the scan passes from pupil 33 to the right portion of iris 31, with the scan showing an increase in voltage level to $V_i$. Lastly, at time $t_4$, the scan passes to the right portion of sclera 29, the voltage level increasing to $V_s$. Therefore, the present invention provides a device with which, eye movement, eye lid blink activity and pupil size and reactivity can therefore be quantitatively and qualitatively analyzed in light of known standards.

We claim:

1. An apparatus for monitoring physiological data of a human subject to detect drug impairment comprising:
   (a) a viewport housing having a viewport shield and first and second interior chambers separated by an opaque member, each chamber adapted to be adjacent an eye of the subject;
   (b) sealing means for excluding substantially all ambient light from impinging upon the eyes of the subject, said sealing means being coupled about the viewport shield;
   (c) energy absorbing means for absorbing energy radiated in the infrared range of the spectrum disposed upon the surfaces of the interior chambers and the opaque member;
   (d) directed infrared source means for radiating energy in the infrared range of the spectrum at target areas of the eyes of the subject and mounted within each of said first and second interior chambers; and
   (e) video sensing means for sensing images of the subject's eye illuminated by radiation in the infrared range of the spectrum mounted within each of the first and second interior chambers.

2. An apparatus for monitoring physiological data defined in claim 1 wherein said video sensing means comprises video cameras sensitive to infrared radiation, each of said video cameras being positioned to minimize the effects of cosine compression.

3. An apparatus for monitoring physiological data as defined in claim 2 wherein said video sensing means is laterally displaced relative to said opaque member and said directed infrared source means.

4. An apparatus for monitoring physiological data as defined in claim 3 wherein each of said video cameras are laterally displaced by 20° of arc from said opaque member.

5. An apparatus for monitoring physiological data as defined in claim 1 wherein said directed infrared source means comprises a plurality of infrared, light emitting diodes.

6. An apparatus for monitoring physiological data as defined in claim 5 wherein said light emitting diodes emit a point source of infrared radiation directed at a portion of the eye of the subject outside of the area of interest sensed by said video sensing means.

7. An apparatus for monitoring physiological data as defined in claim 1 further including first and second illuminating source means for radiating a source of light in the visible portion of the spectrum at the eye of the subject, said illuminating source means being coupled within said first and second interior chambers.

8. An apparatus for monitoring physiological data as defined in claim 1 further including:
   (a) video conversion means for converting the output of said video sensing means into indicia responsive to the images sensed by said video sensing means;
   (b) digital processing means coupled to said video conversion means for recording and comparing the output of said video conversion means to stored standards; and
   (c) video monitoring means coupled to said digital processing means for exhibiting stored data.

9. An apparatus for monitoring physiological data of a human subject to detect drug impairment comprising:
   (a) a viewport housing having a viewport shield and first and second interior chambers separated by a visually opaque member, each chamber adapted to circumscribe and be adjacent to an eye of the subject;
   (b) sealing means for excluding substantially all ambient light from impinging upon the eyes of the subject, said sealing means being coupled about the viewport shield;
   (c) energy absorbing means for absorbing energy radiated in the infrared range of the spectrum disposed upon the surfaces of the interior chambers and the visually opaque member;
   (d) directed infrared source means for radiating energy in the infrared range of the spectrum at target areas of the eyes of the subject and mounted within each of said first and second interior chambers;
   (e) first and second illuminating source means for radiating a source of light in the visual portion of the spectrum at the eye of the subject, said first and second illuminating source means being coupled within said first and second interior chambers respectively; and
   (f) first and second video cameras sensitive to infrared radiation being mounted within said first and second interior chambers respectively, said video cameras being laterally displaced relative to said visually opaque member and said directed infrared source means whereby the effects of cosine compression are minimized.

10. An apparatus as defined in claim 9 wherein said video cameras are laterally displaced by 20° of arc from said visually opaque member.

11. An apparatus for monitoring physiological data as defined in claim 9 wherein said directed infrared source means emit a point source of infrared radiation directed at a portion of the eye of the subject outside of the area of interest sensed by said video sensing means.

* * * * *